(12) United States Patent
Kaald

(10) Patent No.: US 10,251,624 B2
(45) Date of Patent: Apr. 9, 2019

(54) DELTA-SIGMA BEAMFORMER AND METHOD FOR BEAMFORMING

(71) Applicant: General Electric Company, Schenectady, NY (US)

(72) Inventor: Rune Kaald, Oslo (NO)

(73) Assignee: General Electric Company, Schenectady, NY (US)

( * ) Notice: Subject to any disclaimer, the term of this patent is extended or adjusted under 35 U.S.C. 154(b) by 335 days.

(21) Appl. No.: 15/182,757

(22) Filed: Jun. 15, 2016

(65) Prior Publication Data

US 2017/0360400 A1 Dec. 21, 2017

(51) Int. Cl.
*A61B 8/00* (2006.01)
*A61B 8/08* (2006.01)
*A61B 8/14* (2006.01)
*H03M 3/00* (2006.01)

(52) U.S. Cl.
CPC ............ *A61B 8/4494* (2013.01); *A61B 8/145* (2013.01); *A61B 8/4427* (2013.01); *A61B 8/4472* (2013.01); *A61B 8/461* (2013.01); *A61B 8/467* (2013.01); *A61B 8/5207* (2013.01); *H03M 3/462* (2013.01)

(58) Field of Classification Search
None
See application file for complete search history.

(56) References Cited

U.S. PATENT DOCUMENTS

| | | | | |
|---|---|---|---|---|
| 5,964,708 A * | 10/1999 | Freeman | ............. | G01S 7/52028 600/447 |
| 6,366,227 B1 | 4/2002 | Rigby | | |
| 6,867,720 B1 * | 3/2005 | Freeman | ............. | G01S 7/52028 341/143 |
| 7,199,738 B2 | 4/2007 | Han et al. | | |
| 2003/0097071 A1 * | 5/2003 | Halmann | ................. | A61B 8/14 600/459 |
| 2014/0148699 A1 * | 5/2014 | Shim | .................... | A61B 8/4411 600/441 |
| 2015/0340023 A1 | 11/2015 | Hemmsen et al. | | |

OTHER PUBLICATIONS

Hao, Efficient Sigma-Delta beamforming technique for ultrasound imaging, School of Electrical and Electronic Engeneering, 2009 (Year: 2009).*

Freeman et al, "An Ultrasound Beamformer Using Oversampling," 1997 IEEE Ultrasonics Symposium Proceedings; pp. 1687-1690.

* cited by examiner

*Primary Examiner* — Hovhannes Baghdasaryan

(57) ABSTRACT

A delta-sigma beamformer includes a beamsummer and a plurality of delta-sigma modules. Each of the delta sigma modules includes a delta-sigma modulator configured to receive analog ultrasound signals from one or more transducer elements and output a delay line including a plurality of samples based on the analog ultrasound signals. Each delta-sigma modulator includes a comb filter connected to the delta-sigma modulator and configured to output a difference between two of the plurality of samples in the delay line. Each delta-sigma modulator includes an accumulator module. Each accumulator module includes an accumulator connected to the comb filter. Each accumulator module is configured to integrate signals received from the comb filter during a non-delay-expansion period and transmit the integrated signals to the beamsummer during the non-delay-expansion period. Each accumulator module is configured to output a zero to the beamsummer during a delay-expansion period.

20 Claims, 7 Drawing Sheets

DELTA-SIGMA BEAMFORMER AND METHOD FOR BEAMFORMING

FIELD OF THE INVENTION

This disclosure relates generally to a delta-sigma beamformer, an ultrasound imaging system including a delta-sigma beamformer, and a method for beamforming using a delta-sigma beamformer.

BACKGROUND OF THE INVENTION

Many probes used for ultrasound imaging, particularly those probes with a 2D matrix array, such as those currently used for 3D/4D imaging, have arrays with a large number of discrete transducer elements. For example, many conventional probes using a 2D matrix array have more than 1,000 transducer elements. There are significant design constraints associated with the probe cable used to transmit signals from the elements to a beamformer on the system-side for the generation and display of images based on the ultrasound data.

Conventional probe cables require a separate lead or wire to transmit the signal associated with each unique channel. For example, if the ultrasound system has 256 channels, the probe cable will require 256 separate leads. It is not practical or economical to have an individual lead for each element for a contemporary probe with a 2D matrix array, which may have several thousand elements. Adding additional leads to a probe cable significantly increases the cost of the probe cable, and it results in a thicker, heavier, bulkier, less flexible probe cable. It is desirable to keep the probe cable relatively light, thin, and flexible in order to make scanning as ergonomic as possible for clinicians.

Due to the increasing number of transducer elements in contemporary probes and due to the aforementioned desired characteristics for probe cables, there is a significant incentive to perform an analog-to-digital conversion and at least some partial beamforming within the probe in order to reduce the number of channels required to transfer the signals from the probe to the system-side of the ultrasound imaging system.

It is desirable to use an analog-to-digital converter with a relatively broad dynamic range and a high temporal resolution. In order to make the probe ergonomic, it is desirable to minimize the overall size of the probe. Additionally, power use and resulting heat generation are always of concern for probes. As such, it is desirable to use a component for the analog-to-digital conversion that is relatively compact and efficient from a power consumption perspective. A delta-sigma modulator is an analog-to-digital converter that meets the above-stated needs very well.

However, a delta-sigma modulator requires sampling that is uniform in time. This condition is not met during delay-expansion periods, such as when performing dynamic receive focusing. The use of conventional techniques with delta-sigma modulators results in unwanted noise due to some samples being repeated multiple times during delay expansion periods. The high levels of noise due to non-uniform sampling in time have made it difficult or impossible to leverage the high sampling frequency and low power consumption of delta-sigma modulators for analog-to-digital conversion within probes used for ultrasound imaging. Therefore, a delta-sigma beamformer, an ultrasound imaging system, and a method for beamforming using delta-sigma modulators is desired for at least the reasons discussed hereinabove.

BRIEF DESCRIPTION OF THE INVENTION

The above-mentioned shortcomings, disadvantages, and problems are addressed herein, which will be understood by reading and understanding the following specification.

In an embodiment, a delta-sigma beamformer includes a beamsummer and a plurality of delta-sigma modules. Each of the delta-sigma modules includes a delta-sigma modulator configured to receive analog ultrasound signals from one or more transducer elements and to output a delay line including a plurality of samples based on the analog ultrasound signals. Each delta-sigma modulator includes a comb filter connected to the delta-sigma modulator and configured to output a difference between two of the plurality of samples in the delay line. Each delta-sigma modulator includes an accumulator module. Each accumulator module includes an accumulator connected to the comb filter. Each accumulator is configured to integrate signals received from the comb filter during a non-delay-expansion period and transmit the integrated signals to the beamsummer during the non-delay-expansion period. Each accumulator module is configured to output a zero to the beamsummer during a delay-expansion period.

In an embodiment, an ultrasound imaging system includes a display screen, a beamsummer, a plurality of transducer elements arranged in an array, a plurality of channels, where each of the channels is configured to carry signals from one or more of the plurality of transducer elements, and a plurality of delta-sigma modules. Each of the delta-sigma modules is connected to one of the plurality of channels and includes a delta-sigma modulator configured to receive analog ultrasound signals from one or more of the plurality of channels and to output a delay line including a plurality of samples based on the analog ultrasound signals. Each delta-sigma module includes a comb filter connected to the delta-sigma modulator and configured to output a difference between two of the plurality of samples in the delay line. Each delta-sigma modulator includes an accumulator module. The accumulator module includes an accumulator connected to the comb filter. The accumulator module is configured to integrate signals received from the comb filter during a non-delay-expansion period and transmit the integrated signals to the beamsummer during the non-delay-expansion period. The accumulator module is configured to output a zero to the beamsummer during a delay-expansion period.

In an embodiment, a method for beamforming ultrasound signals includes providing analog ultrasound signals from a plurality of transducer elements to a delta-sigma modulator associated with one of a plurality of channels. The method includes outputting a delay line from the delta-sigma modulator, the delay line including a plurality of samples based on the analog ultrasound signals. The method includes outputting, with a comb filter, a plurality of differences between samples at two different locations in the delay line. The method includes providing the plurality of differences to an accumulator during a non-delay-expansion period. The method includes generating an output signal with the accumulator during the non-delay-expansion period, where the output signal comprises an integration based on the plurality of differences. The method includes providing the output signal to a beamsummer during the non-delay-expansion period. The method includes activating a switch during a delay-expansion period, where activating the switch stops the plurality of differences from being sent to the accumulator during the delay-expansion period and causes a value of zero to be sent to the beamsummer during the delay expansion period. The method includes generating an image based on both the output signal and the value of zero provided to the beamsummer and displaying the image.

Various other features, objects, and advantages of the invention will be made apparent to those skilled in the art from the accompanying drawings and detailed description thereof.

DETAILED DESCRIPTION OF THE INVENTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical, and other changes may be made without departing from the scope of the embodiments. The following detailed description is, therefore, not to be taken as limiting the scope of the invention.

Figure 1:
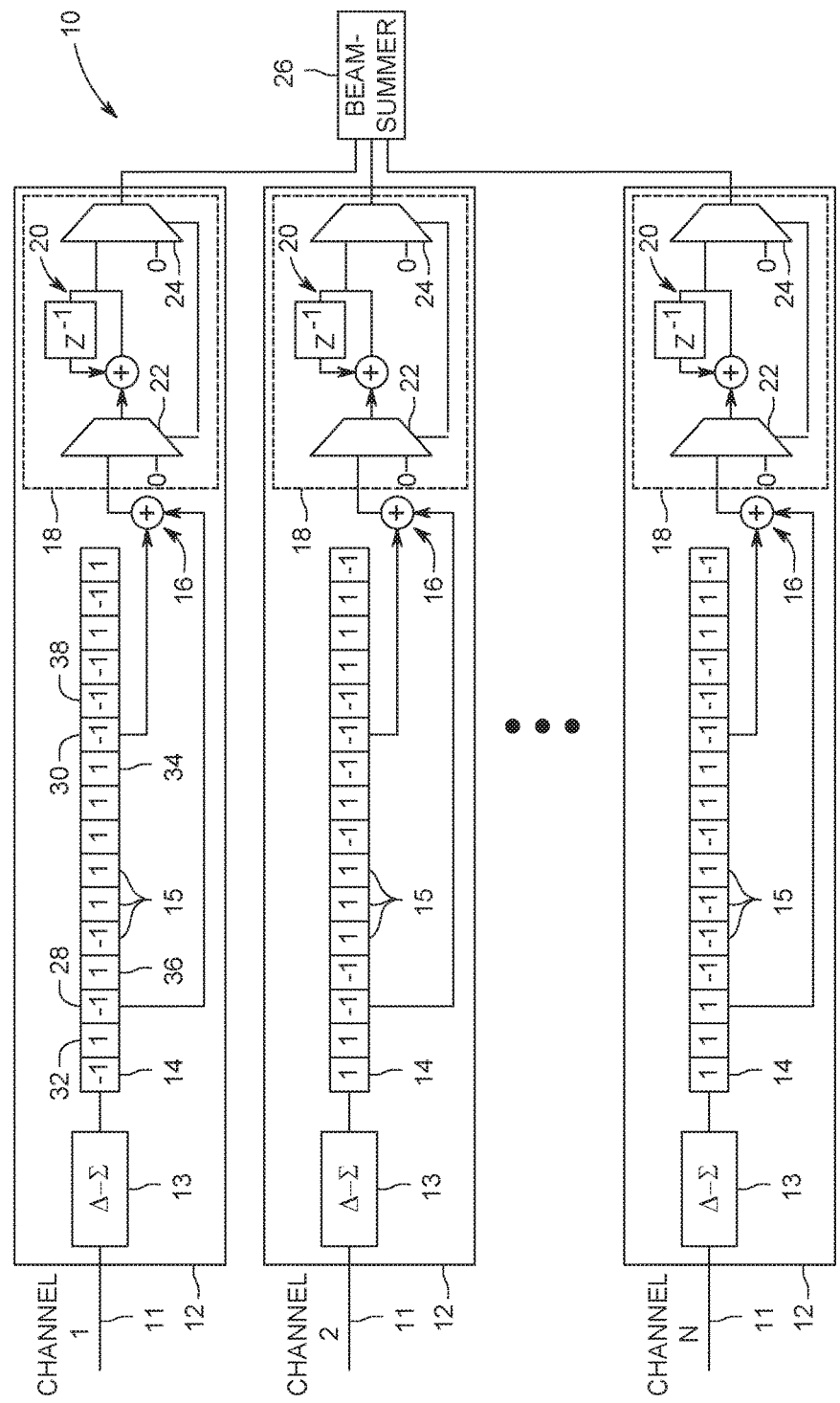
FIG. 1 is a schematic diagram of a delta-sigma beam-former in accordance with an embodiment.

FIG. 1 is a schematic representation of a delta-sigma beamformer 10 in accordance with an embodiment. The delta-sigma beamformer 10 includes a plurality of channels 11. FIG. 1 specifically shows channel 1, channel 2, and channel N, with the understanding that the beamformer 10 may include N separate channels, where N is a positive integer. Each of the channels 11 carries ultrasound signals from one or more transducer elements (not shown in FIG. 1). According to an exemplary embodiment, there are identical hardware components associated with each of the channels in the delta-sigma beamformer 10. The identical components may be configured to perform substantially identical functions for each of the respective channels in accordance with an embodiment. Identical reference numbers have been used to identify identical components associated with each of the channels in this disclosure.

The delta-sigma beamformer 10 includes a plurality of delta-sigma modules 12. Each of the delta-sigma modules 12 includes a delta-sigma modulator 13. Each delta-sigma modulator 13 is an analog-to-digital converter that is adapted to convert an analog ultrasound signal associated with each respective channel into a delay line 14, which is a type of digital signal. Delta-sigma modulators have a higher temporal resolution than most other types of analog-to-digital converters used in conventional beam-formers. This allows the data rate of the signals represented in each of the delay lines 14 to easily exceed the Nyquist sampling frequency of the analog ultrasound signal received from the one or more transducer elements. For example, the sampling frequency of a single-bit delta-sigma modulator is approximately 32 times higher than an otherwise equivalent conventional analog-to-digital converter. Additionally, the delta-sigma modulators 13 use relatively less power than most other types of analog-to-digital converters used in conventional beamformers. This helps minimize total power consumption of the delta-sigma beamformer 10, which can be a significant advantage for portable or battery powered systems, and is a particularly useful advantage for embodiments where the delta-sigma beamformer 10 is located in a battery-powered wireless probe. Ultrasound probe manufacturers are also concerned with minimizing the temperature of the probe in order to comply with regulatory guidelines limiting the maximum temperatures of the surface of the probe in contact with the patient. By using less total power, the delta-sigma beamformer 10 helps to reduce the temperature of the probe.

Each delay line 14 includes a plurality of samples 15. The delta-sigma modulators 13 may be configured to output either a single-bit delay line or a multi-bit delay line. A single-bit delay line encodes the analog ultrasound signal using just two values, such as 1 and 0 or −1 and 1. The delta-sigma modulators 13 shown in FIG. 1 output single-bit delay lines using the values of −1 and 1. A multi-bit delay line uses more than two discrete values to encode the analog ultrasound signal. For example, a multi-bit delay line may use values of −1, 0, and 1 to encode the analog ultrasound signal.

The delta-sigma beamformer 10 includes a plurality of comb filters 16 and a plurality of accumulator modules 18. The comb filter 16 receives samples from two different locations in the delay line 14 as an input and outputs a difference between the two samples. The comb filter 16 will be described in more detail hereinafter.

The delta-sigma beamformer 10 includes a plurality of accumulator modules 18. According to an exemplary embodiment, each accumulator module 18 includes an accumulator 20, a first multiplexer 22, and a second multiplexer 24. The delta-sigma beamformer 10 also includes a beamsummer 26 connected to each of the accumulator modules 18.

Each delta-sigma modulator 13 may receive analog ultrasound signals from a single transducer element or from a plurality of transducer elements. Since the delta-sigma beamformer 10 is particularly advantageous for systems with a large number of transducer elements, channels on many embodiments will receive analog ultrasound signals from a plurality of transducer elements. According to one exemplary embodiment, the transducer elements may be organized into a plurality of sub-apertures, or SAPs. Each SAP includes a plurality of transducer elements. The transducer elements in each SAP may be steered and focused as a group. However, according to other embodiments, the individual transducer elements in each SAP may be independently steered and focused as well. Organizing the transducer elements in SAPs helps to reduce the number of channels needed to transmit ultrasound signals from the probe. Sub-aperture processing is known by those skilled in the art.

In other embodiments, the transducer elements may not be arranged into SAPs. In these embodiments, each channel 11 may carry ultrasound signals from a single transducer element.

Each delta-sigma modulator 13 received the analog ultrasound signal as an input and outputs a digital ultrasound signal, represented as the delay line 14 in FIG. 1. While actively receiving ultrasound data, each delta-sigma modulator 13 converts the analog ultrasound signal from the transducer element or elements into a digital ultrasound signal in real-time. The digital ultrasound signal output by each delta-sigma modulator 13 is represented by the delay line 14. While receiving ultrasound data, each delta-sigma modulator 13 outputs data in the delay line 14 at the sample frequency governed by the time resolution of the delta-sigma modulator 13. Additional details about the delta-sigma beamformer 10 will be discussed with respect to the method shown in FIG. 2.

Figure 2:
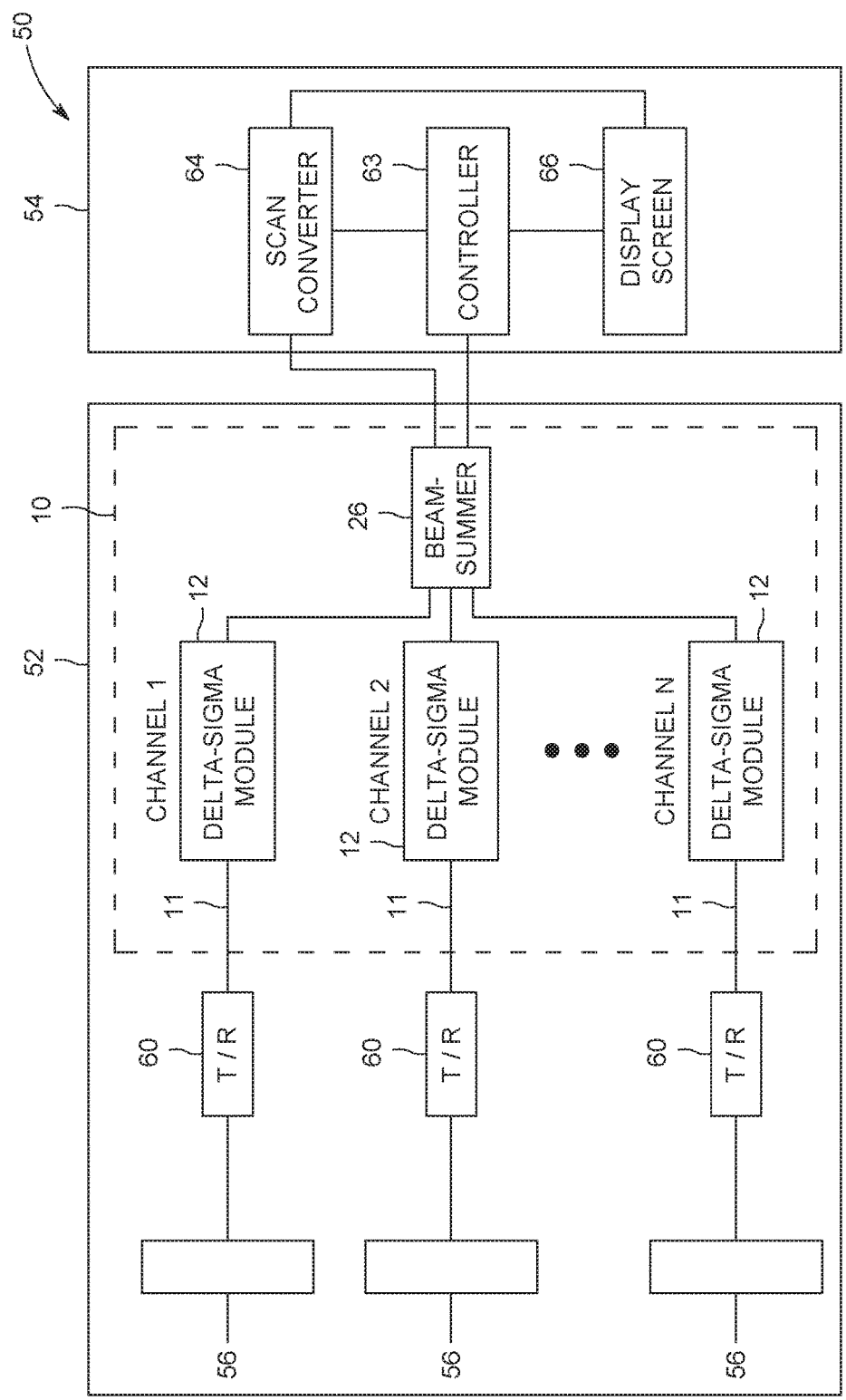
FIG. 2 is a schematic diagram of an ultrasound imaging system in accordance with an embodiment.
Figure 3:
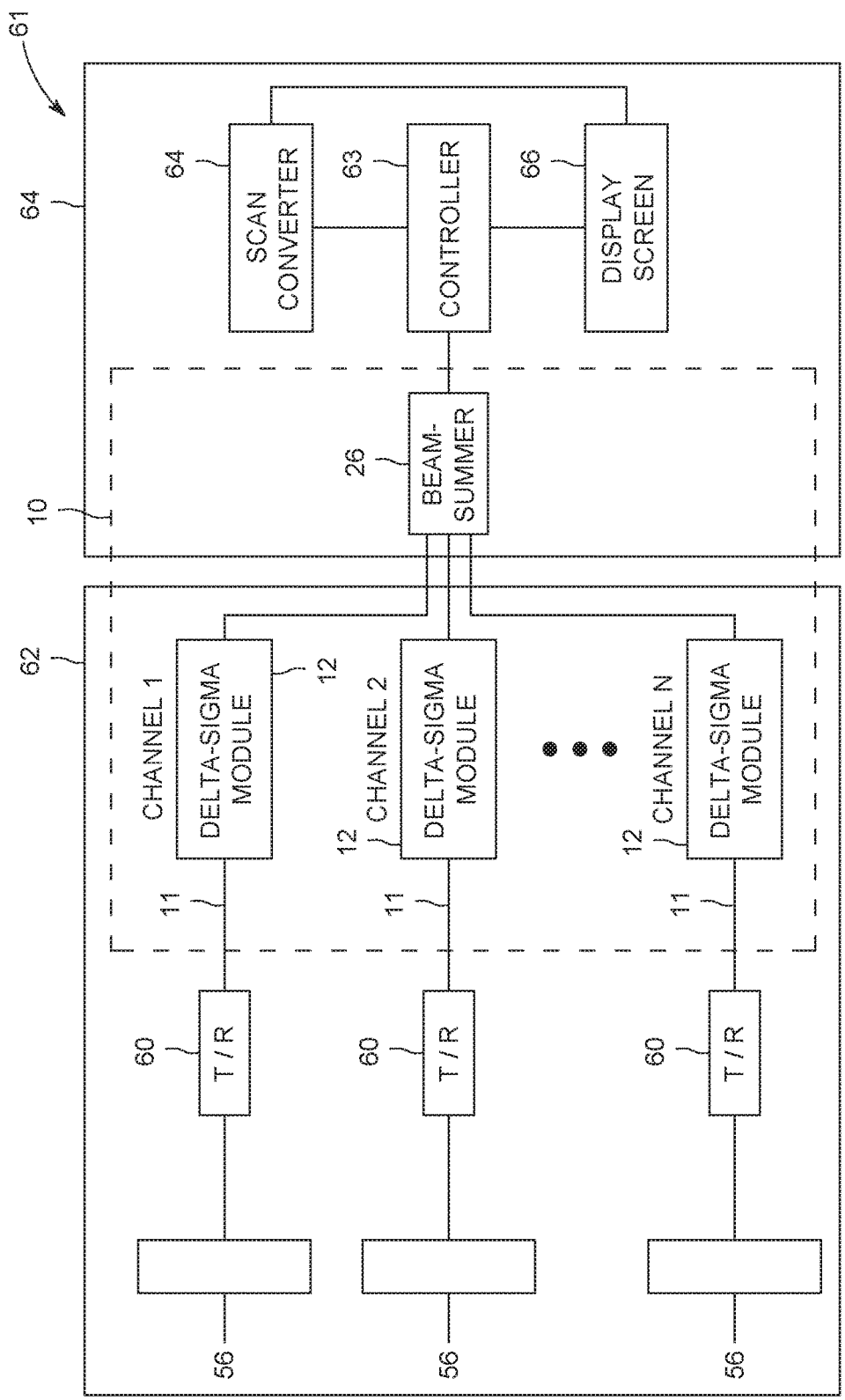
FIG. 3 is a schematic diagram of an ultrasound imaging system in accordance with an embodiment.
Figure 4:
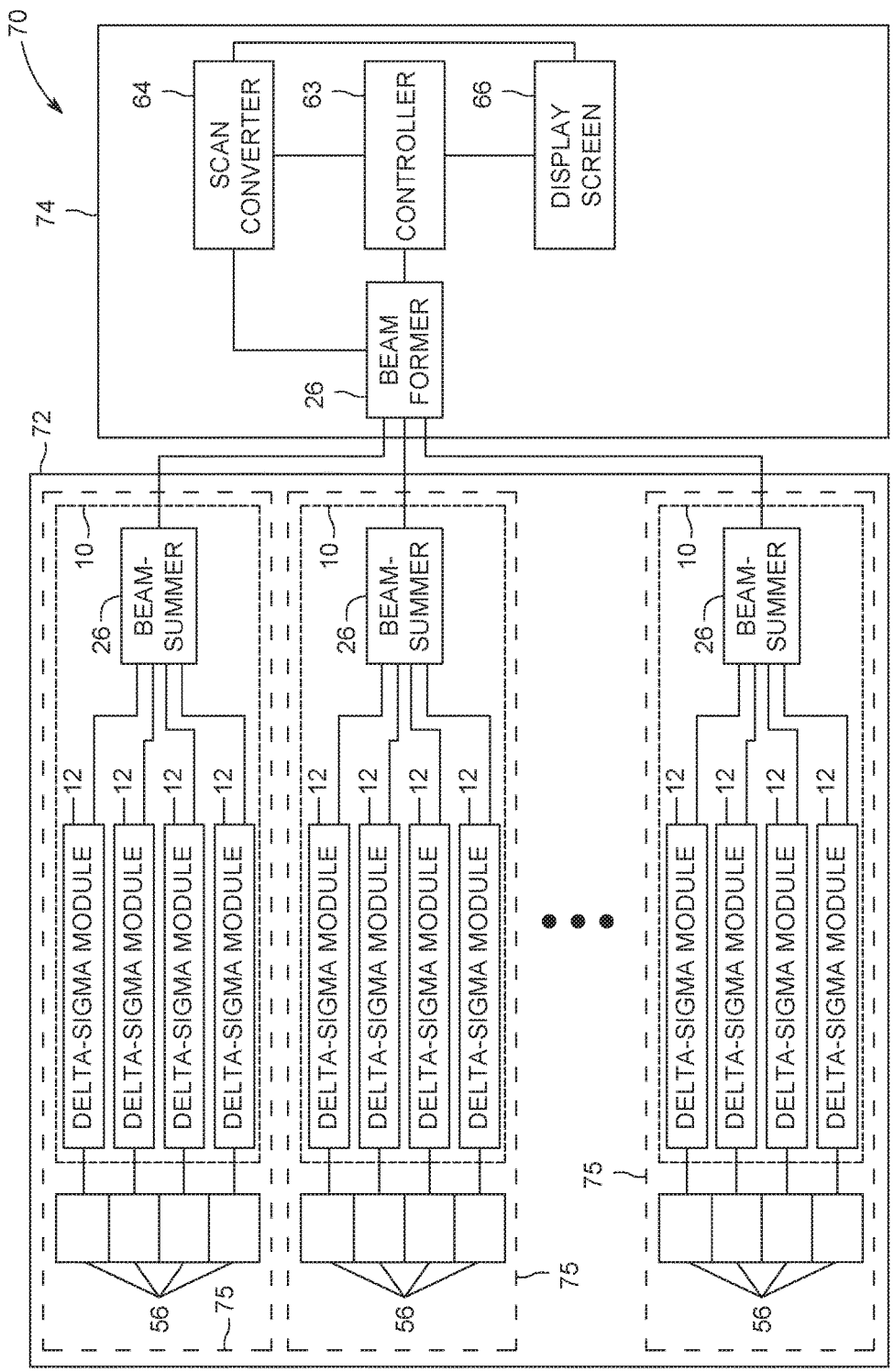
FIG. 4 is a schematic diagram of an ultrasound imaging system in accordance with an embodiment.
Figure 5:
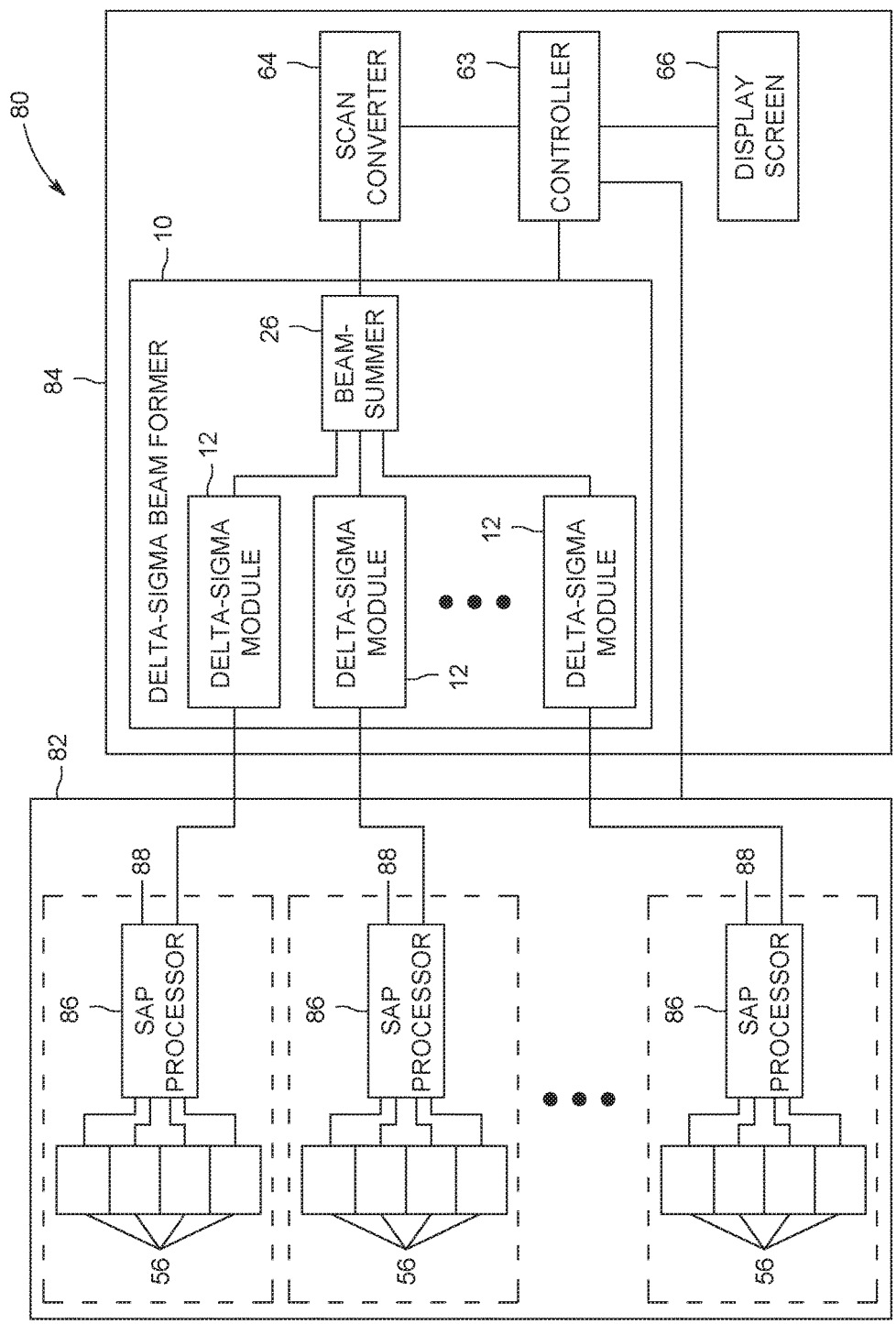
FIG. 5 is a schematic diagram of an ultrasound imaging system in accordance with an embodiment.

FIG. 2 is a schematic representation of an ultrasound imaging system 50 in accordance with an exemplary embodiment. FIG. 3 is a schematic representation of an ultrasound imaging system 61 in accordance with an embodiment. FIG. 4 is a schematic representation of an ultrasound imaging system 70 in accordance with an embodiment. FIG. 5 is a schematic representation of an ultrasound imaging system 80 in accordance with an embodiment. Common reference numbers are to identify identical or substantially identical elements/components in FIGS. 2, 3, 4, and 5.

Referring to FIG. 2, the ultrasound imaging system 50 includes a probe 52 and a main module 54. The ultrasound imaging system 50 also includes the sigma-delta beamformer 10, which was described previously with respect to FIG. 1. The probe 52 includes a plurality of transducer elements 56 arranged in an array. Only channel 1, channel 2, and channel N are represented in FIG. 3, but it should be appreciated that N may be any positive integer according to various embodiments. One or more transducer elements are connected to each of the delta-sigma modules 12. Each transmit-receive switch 60 controls whether each respective element or group of elements are used for transmitting ultrasound energy or receiving ultrasound energy. The sigma-delta beamformer 10 may be completely disposed within the probe 52 according to an embodiment. According to other embodiments, one or more components of the delta-sigma beamformer 10 may be disposed in the main module 54. However, positioning the beamsummer 26 in the probe, as is shown in FIG. 3, allows the probe 52 to transmit fully beamformed ultrasound data to the main module 54.

The main module 54 may be a cart-based main module, a laptop, or a hand-held or hand-carried device, such as a tablet or smartphone. The main module 54 includes a controller 63, a scan converter 64, and a display screen 66. The controller 63 may include a central processor (CPU) according to an embodiment. According to other embodiments, the controller 63 may include other electronic components capable of carrying out processing functions, such as a digital signal processor, a field-programmable gate array (FPGA), a graphic board, or a graphics processing unit (GPU). According to other embodiments, the controller 63 may include multiple electronic components capable of carrying out processing functions. For example, the controller 63 may include two or more electronic components selected from a list of electronic components including: a central processor, a digital signal processor, an FPGA, a graphic board, and a GPU. The controller 63 is connected to the probe 52 and controls the sigma-delta beamformer 10 and the transmit-receive switches 60. The controller 63 also controls the display screen 66 and the scan converter 64. The scan converter 64 receives beamformed ultrasound data from the beamsummer 26 and processes the beamformed ultrasound data for display on the display screen 66. The display screen 66 may comprise a monitor, an LED display, a cathode ray tube, a projector display, or any other type of apparatus configured for displaying an image. The display screen 66 may comprise a touch screen or a multi-touch screen configured to receive user commands and inputs. In other embodiments, the main module may include one or more separate user interface devices (not shown in FIG. 2).

The probe 52 may communicate data to the main module 54 through an electrical connection, such as a probe cable. According to other embodiments, the probe 52 may communicate data wirelessly to the main module 54. According to the embodiment shown in FIG. 3, the probe 52 may communicate beamformed digital ultrasound data to the main module 54.

The ultrasound imaging system 61 shown in FIG. 3 includes a probe 62 and a main module 64. The probe 62 includes transducer elements 56, transmit-receive switches 60, and delta-sigma modules 12. The probe 62 may be a linear array, a phased array, a curved linear array, a 1.25D array, a 1.5D array, a 1.75D array, a 2D matrix array, a mechanically rotating array, or any other type of probe including more than one transducer element. A plurality of channels 11 carry ultrasound signals from each transducer element 56 to each respective delta-sigma module 12. According to the embodiment shown in FIG. 3, a separate delta-sigma module 12 processes the ultrasound signals from each transducer element 56.

The main module 64 includes the beamsummer 26, the controller 63, the scan converter 64 and the display screen 66. In the ultrasound imaging system 61, the delta-sigma beamformer 10 is distributed between the probe 62 and the main module 64. It may be advantageous to locate the beamsummer 26 in the main module 64, as shown in FIG. 3, as opposed to in the probe, as shown in FIG. 2. There are considerably fewer power, heat, and size constraints in the main module 64. In other words, it may be possible to use a bigger, less power efficient beamsummer 26 that generates more heat by locating the beamsummer 26 in the main module 64. As such, it may be possible to use less expensive components for the beamsummer 26 and/or attain higher performance specifications with the beamformer 10.

FIG. 4 is a schematic representation of an ultrasound imaging system 70 in accordance with an exemplary embodiment. The ultrasound imaging system 61 includes a probe 72 and a main module 74. The probe 72 includes transducer elements 56, delta-sigma modules 12, and beamsummers 26. The probe may be a linear array, a phased array, a curved linear array, a 1.25D array, a 1.5D array, a 1.75D array, a 2D matrix array, a mechanically rotating array, or any other type of probe including more than one transducer elements. The transducer elements 56 are arranged into a plurality of SAPs 75. Each SAP 75 includes a plurality of transducer elements 56 and a delta-sigma beamformer 10. There is a delta-sigma module 12 associated with each transducer element 56 in the SAP 75 according to an embodiment. Each delta-sigma beamformer 10 (associated with each SAP 75) performs partial beamforming on the ultrasound signals received by the transducer elements 56. Each SAP 75 may be configured to have a fixed focus for the plurality of transducer elements in the SAP 75, or each SAP 75 may be configured to have dynamically changing focus for the transducer elements in the SAP that tracks with depth. Each SAP 75 may, according to an embodiment, have 32 elements. It should be appreciated that SAPs may have either more than 32 or less than 32 elements according to other embodiments.

The main module 74 includes beamformer 76, scan controller 64, controller 63, and the display screen 66. Each delta-sigma beamformer 10 associated with a respective SAP 75 outputs digital beamformed data from transducer elements 56 in the respective SAP 75. The beamformer 76 in the main module 74 may comprise a conventional beamformer. It is not necessary or desirable for the beamformer 76 to be a delta-sigma beamformer since the data from the plurality of SAPS is already digitized. The beamformer 76 beamforms the digital data from the plurality of SAPS. After beamforming at the beamformer 76, the digital data is scan converted at the scan converter 64 and displayed as an image on the display screen 66.

The embodiment shown in FIG. 4 performs the beamforming in two stages: In a first stage, partial beamforming is performed within each of the SAPs 75. The delta-sigma module 12 in each SAP 75 beamforms the analog ultrasound signals received from the transducer elements in the respective SAP 75. And then, in a second stage, any remaining beamforming is performed in the beamformer 76. The beamformer 76 beamforms the digital signals received from each of the SAPs 75. The two-stage beamforming shown in FIG. 4 is more computationally efficient than performing all the beamforming at once. This allows for either the use of less expensive components and/or for faster clock speeds for performing the complete beamforming of the ultrasound signals. By performing the analog-to-digital conversion in the probe 72, it is possible for the beamformer 76 in the main module 74 to be simpler than it would be if it had to process analog data. Additionally, since each SAP 75 beamforms the signals from a plurality of elements into a single output or channel, it is possible to use a simpler/less expensive connection between the probe 72 and the main module 74 to transmit the partially beamformed data. This further reduces the cost and complexity of the overall ultrasound imaging system 70.

FIG. 5 is a schematic diagram of an ultrasound imaging system 80 according to an exemplary embodiment. The ultrasound imaging system 80 includes a probe 82 and a main module 84. The probe 82 includes transducer elements 56 and a plurality of SAP processors 86. The probe 82 may be a linear array, a phased array, a curved linear array, a 1.25D array, a 1.5D array, a 1.75D array, a 2D matrix array, a mechanically rotating array, or any other type of probe including more than one transducer elements. The transducer elements 56 are arranged into a plurality of SAPs 88. Each SAP 88 includes a plurality of transducer elements 56. The SAP processor 86 may comprise hardware or firmware that performs beamforming on the analog ultrasound signals received from the plurality of transducer elements 56 in each respective SAP 88. According to the embodiment shown in FIG. 5, the SAP processor 86 associated with each SAP 88 outputs analog data.

The main module 84 includes a delta-sigma beamformer 10, scan converter 64, controller 63, and display screen 66. As described above, each SAP processor 86 may output partially beamformed data from the transducer elements 56. Each SAP 88 may output the partially beamformed data (which is still analog data) to a unique one of the plurality of delta-sigma modules 12 located in the delta-sigma beamformer 10. The delta-sigma beamformer 10 converts the partially beamformed data from analog into digital data and completes the beamforming. The beamformed data is pushed from the delta-sigma beamformer 10 to the scan converter 64, where it is converted into a format for display on the display screen 66.

Figure 6:
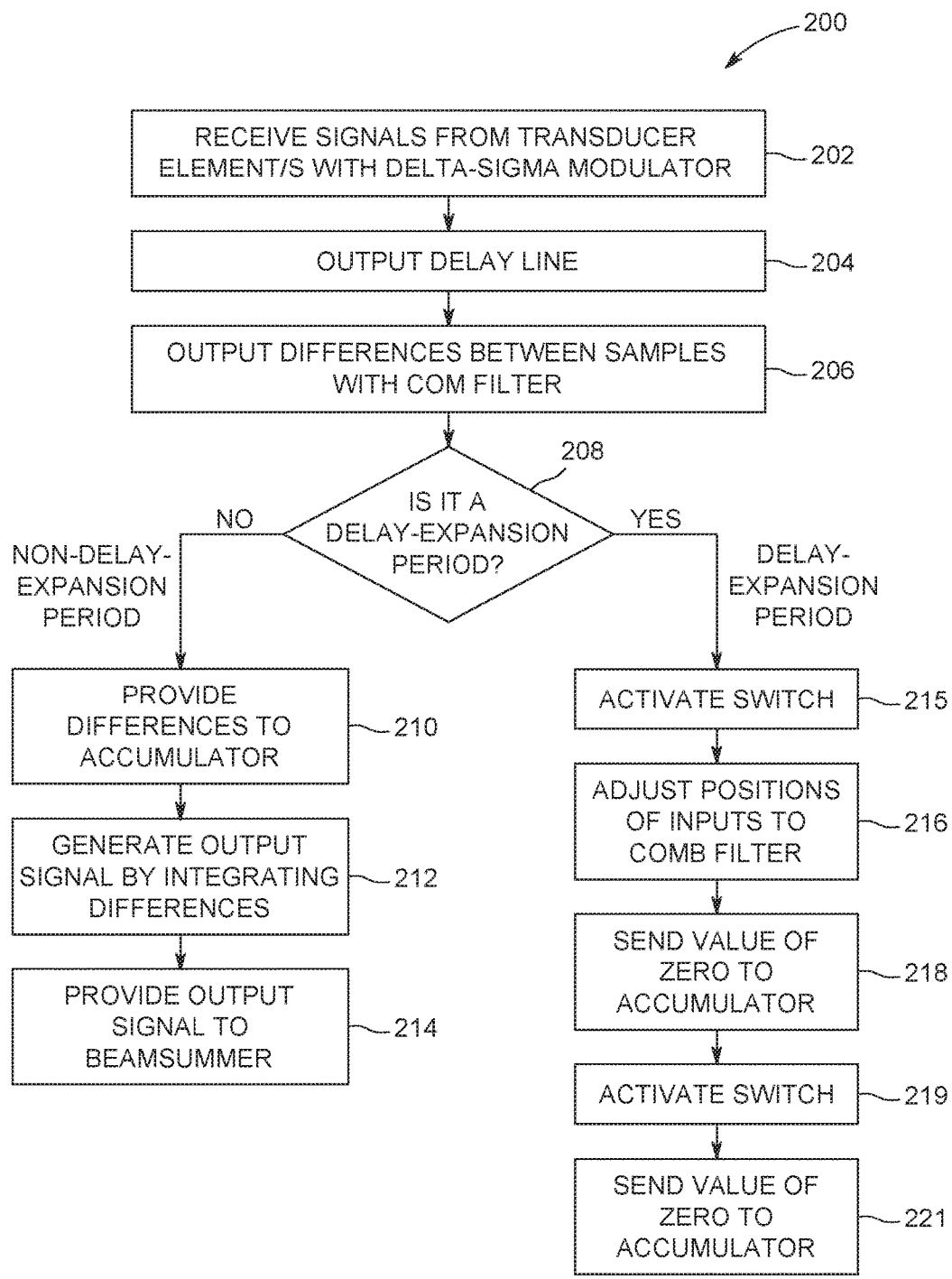
FIG. 6 is a flow chart of a method in accordance with an embodiment.

FIG. 6 is a flow chart of a method 200. The individual blocks of the flow chart represent steps that may be performed in accordance with the method 200. Additional embodiments may perform the steps shown in a different sequence and/or additional embodiments may include additional steps not shown in FIG. 6. The method 200 represents steps that may be performed within an individual beamforming module, such as the beamforming module 12 shown in FIG. 1. The technical effect of the method 200 is providing either an output signal or a value of zero to a beamsummer. The method 200 will be described using the delta-sigma module 12 shown in FIG. 1 in accordance with an exemplary embodiment. It should be appreciated that the method 200 may be performed using delta-sigma modules that are configured differently than the delta-sigma module 12 shown in FIG. 1.

At step 202, the delta-sigma modulator 13 within one of the delta sigma modules 12 receives analog ultrasound signals on one of the channels 11. The channel 11 may contain analog ultrasound signals from one or more transducer elements 56 (not shown in FIG. 1). At step 204, each of the delta-sigma modulators 13 outputs delay line 14 in response to receiving the analog ultrasound signal from one or more transducer elements. Each delta-sigma modulator 13 outputs delay line 14 at the sampling frequency determined by the time resolution of the delta-sigma modulator 13. The delay line 14 represents a digitization of the received analog ultrasound signals.

At step 206, the comb filter 16 outputs the difference between two samples at two different locations in the delay line 14. Focusing on the comb filter 16 associated with channel 1, the comb filter 16 receives inputs from two distinct locations in the delay line 14. For example, the comb filter 16 associated with channel 1 may receive inputs from a first location 28 and a second location 30 in the delay line 14. As described above, the values of the samples at the first location 28 and the second location 30 in the delay line 14 are updated at the sampling frequency of the delta-sigma modulator 13.

The first location 28 is separated from the second location 30 by 7 samples according to the embodiment of FIG. 1. It should be appreciated that the first location may be separated from the second location by either more than 7 samples or fewer than 7 samples according to other embodiments.

At step 208 of the method 200, it is determined if the delta-sigma module 12 is currently in a delay-expansion period. A non-delay-expansion period corresponds to a period of time when the receive focus as controlled by the delta-sigma module 12 is not changing. (i.e., a period when dynamic receive focusing is not currently being used). In contrast, a delay-expansion period corresponds to a period of time when the dynamic receive focusing is actively being used to change the focus with the delta-sigma module 12 while receiving ultrasound data. The distance in the delay line 14, such as the number of samples between the first location 28 and the second location 30, may be adjusted during the delay-expansion period, as will be described hereinafter.

If it is not a delay-expansion period (i.e., it is a non-delay-expansion period) the method 200 advances to step 210. During a non-delay-expansion period, the positions of the two inputs to the comb filter 16 may remain fixed. For example, the inputs to the comb filter 16 may remain at the first location 28 and the second location 30 (with a 7 sample gap between the first location 28 and the second location 30) during the non-delay-expansion period. As described above, the samples in the delay line 14 are updated at the sampling frequency of the delta-sigma modulator 13. Updated values are input into the comb filter 16 from the first location 28 and the second location 30 as the samples in the delay line 14 are updated.

At step 210, the differences between the two samples, such as the difference between the sample from the first location 28 and the sample from the second location 30 are provided to the accumulator 20. According to an embodiment, the comb filter 16 determines the differences between the sample at the first location 28 and the sample at the second location 30. Since the samples are updated at the sampling frequency of the delta-sigma modulator 13, over time, the comb filter 16 provides a plurality of differences to the accumulator 20 as the samples in the delay line 14 are updated. Next, at step 212, the accumulator 20 integrates, or sums, the plurality of differences between the samples in the delay line 14 that are provided by the comb filter 16. The accumulator 20 provides an output signal to the beamsummer 26 at step 214. During non-delay-expansion periods, the output signal comprises an integration of the differences between the sample at the first location 28 and the sample at the second location 30. The samples in the output signal are updated at the same sampling frequency as the associated delta-sigma modulator 13.

Signals from each of the other channels are processed in a manner similar to channel 1 described hereinabove. FIG. 1 schematically represents a beamformer with N separate channels. Those skilled in the art should appreciate that the beamformer 10 will process the signals from channels 2 through N in a manner similar to that which was described with respect to channel 1. At step 214, output signals from each of the plurality of accumulator modules 18 are provided to the beamsummer 26.

If at step 208, it is a delay-expansion period, such as when in the process of performing dynamic receive focusing, the method 200 advances to step 215 from step 208. At step 215, a switch is activated. According to an embodiment, the switch may be the first multiplexer 22. At step 216, during a delay-expansion period, the comb filter 16 is adjusted so that the samples are received from different locations in the delay line 14. For examples, the first input to the comb filter 16 may be obtained from location 32 instead of the first location 28, and the second input to the comb filter 16 may be obtained from location 34 instead of the second location 30 when shifting the inputs to the left. When shifting the inputs to the right, the first input to the comb filter 16 may be obtained from location 36 instead of the first location 28, and the second input to the comb filter 16 may be obtained from location 38 instead of the second location 30. Shifting the inputs to the comb filter 16 to the left in the delay line 14 (i.e., closer to the delta-sigma modulator 13) results in less of a delay for that particular channel, whereas shifting the inputs to the comb filter 16 to the right (i.e., further away from the delta-sigma modulator 13) results in a greater delay for that particular channel. Additionally, in some embodiments, the spacing between locations of the two samples in the delay line 14 that are used as inputs to the comb filter 16 may be adjusted. For example, the comb filter 16 may be adjusted so as to move from a distance of 7 samples between the two locations in the delay line 14 (as shown in FIG. 1) to a distance of less than 7 samples between the two locations in the delay line 14. For example, the comb filter 16 may be adjusted so that there is a distance of 6 or fewer samples between the two locations in the delay line 14 used as inputs to the comb filter 16. Additionally, the comb filter 16 may be adjusted so as to move from a distance of 7 samples between the two locations in the delay line 14 (as shown in FIG. 1) to a distance of greater than 7 samples between the two locations in the delay line 14. For example, the comb filter 16 may be adjusted so that there is a distance of 8 or more samples between the two locations in the delay line 14 used as inputs to the comb filter 16. According to an embodiment, the distance between the samples in the delay line 16 may be adjusted to a longer distance in order to attenuate unwanted noise when performing dynamic focusing at deeper depths. Additionally, a shorter distance between the two samples may be used when performing dynamic focusing at shallower depths. It should be appreciated that not all embodiments may adjust the distance between the samples in the delay line 14 used as inputs to the comb filter. Many embodiments may keep the distance between the samples fixed in the delay line 14 and just shift the positions of the samples that are used as inputs to the left or the right in the delay line 14.

At step 218, the first multiplexer 22 outputs a value of zero, which is sent to the accumulator 20 during delay-expansion periods. The first multiplexer 22 is configured to output a value of zero to the accumulator 20 when the switch is activated at step 215. At step 219, a second switch, such as the second multiplexer 24 is activated, and, at step 221, a value of zero is output to the beamsummer 26 during delay-expansion periods. By providing a zero to the accumulator 20 during delay-expansion periods, the first multiplexer 22 prevents the accumulator 20 from receiving duplicate samples from the delay line 14 (output by the delta-sigma modulator 13) during a delay-expansion period. Additionally, the second multiplexer 24 outputs a zero to the beamsummer 26 during delay-expansion periods. This prevents the beamsummer 26 from summing duplicate values during a delay-expansion period. Summing duplicate values from the delay line 14 would otherwise result in the introduction of unwanted noise in an image generated from the beamsummed data. The first multiplexer 22 and the second multiplexer 24 are just two examples of switches that may be used in the accumulator module 18 to control the input to the accumulator 20 and the output from the accumulator 20 during delay-expansion periods. It should be appreciated that different types of circuits, mechanisms, or logic may be used to control the output to the accumulator 20 and from the accumulator 20 during delay-expansion periods according to other embodiments.

In accordance with an embodiment, the method 200 may be performed with each of the plurality of delta-sigma modules 12. As described hereinabove, each of the delta-sigma modules may be associated with a single transducer element or a group of transducer elements. Implementing the method 200 with each delta-sigma module 12 results in the generation of digital ultrasound data that is at least partially beamformed after being processed by the delta-sigma modules 12 and the beamsummer 26.

The method 200 provides a number of advantages over conventional beamforming techniques. The delta-sigma modulators 13 are faster than convention analog-to-digital converters. This provides a data stream with high temporal resolution, which results in the need to do less interpolation between samples, and ultimately results in higher image quality, particularly at higher frame rates.

The delta-sigma modulator is very power efficient, which results in lower power consumption, which is particularly important for portable or battery powered probes. The high temporal resolution, combined with the low power consumption of the delta-sigma modulators 13 allows for the analog signal to be converted to digital earlier in the processing chain, such as in the probe. For systems where the probe is connected to the rest of the system by a cable, this reduces the number of wires or leads needed to transmit the ultrasound signal, assuming that each delta-sigma modulator 13 converts signals from multiple elements. Additionally, it is computationally more efficient to process the digital signal, so converting the signal earlier in the processing chain, reduces the hardware demands if additional processing is required. controller 63 controller 63 controller 63 controller 63 controller 63 controller 63 controller 63

Figure 7:
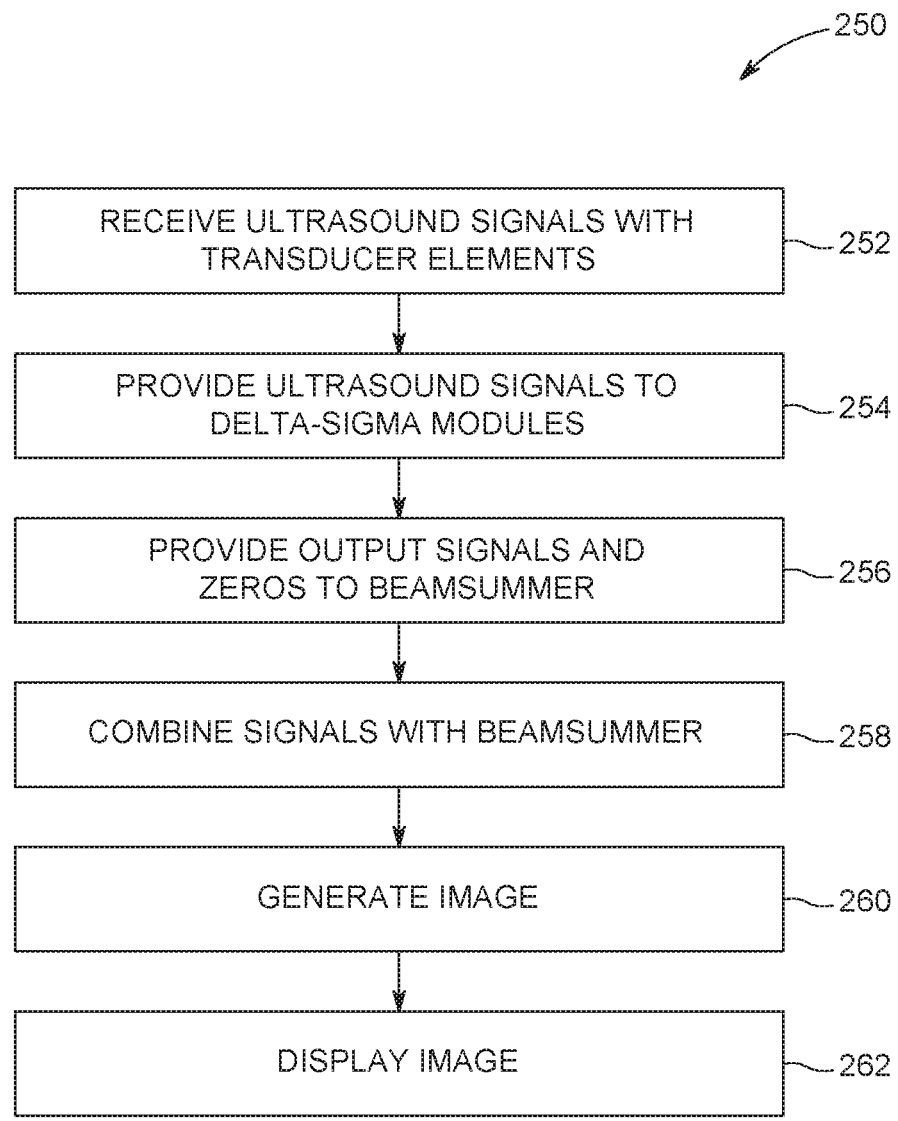
FIG. 7 is a flow chart of a method in accordance with an embodiment.

FIG. 7 is a flow chart of a method 250. The individual blocks of the flow chart represent steps that may be performed in accordance with the method 250. Additional embodiments may perform the steps shown in a different sequence and/or additional embodiments may include additional steps not shown in FIG. 7. The method 250 represents steps that may be performed within an ultrasound imaging system, such as the ultrasound imaging system 50 shown in FIG. 2. The technical effect of the method 250 is displaying an image generated with a delta-sigma beamformer. The method 250 will be described using the delta-sigma module 12 shown in FIG. 1 and the ultrasound imaging system 50 shown in FIG. 2 in accordance with an exemplary embodiment. It should be appreciated that the method 250 may be performed using delta-sigma modules that are configured differently than the delta-sigma module 12 shown in FIG. 1.

At step 252, analog ultrasound signals are received with the transducer elements 56 (shown in FIG. 2). At step 254, the analog ultrasound signals are provided to the delta-sigma modules 12. Each delta-sigma module 12 converts the analog ultrasound signals to digital data. Each delta-sigma module 12 may, for instance, convert the analog ultrasound signals to digital data in the manner described with respect to the method described in FIG. 6. At step 256, each of the delta-sigma modules 12 provides the output signals or zeros to the beamsummer 26 according to the technique described with respect to FIG. 6. For example, if the particular delta-sigma module 12 is in a delay-expansion period, it will output a zero to the beamsummer 26. On the other hand, if the particular delta-sigma module 12 is in a non-delay-expansion period, the delta-sigma module 12 will output a combined signal to the beamsummer 26. At step 258, signals from the various delta-sigma modules 12 are combined with the beamsummer 26. Steps 252, 254, 256, and 258 may be iterated multiple times in order to acquire ultrasound data at different depths. After steps 252, 254, 256, and 258 have been performed enough times to acquire a whole image, at step 260, the method 250 generates an image based on the combined signals and zeros provided by the plurality of delta-sigma modules 12 over time. At step 262 the image is displayed. The image may, for instance, be displayed on display screen 66 (shown in FIG. 3) according to an embodiment. The image may be a 2D image, a 3D image, a Doppler image, a colorflow image, or any other mode of image. The image may comprise a still image or a live or real-time image.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

I claim:

1. A delta-sigma beamformer comprising:
   a beamsummer; and
   a plurality of delta-sigma modules, each of the delta-sigma modules comprising:
      a delta-sigma modulator configured to receive analog ultrasound signals from one or more transducer elements and output a delay line including a plurality of samples based on the analog ultrasound signals;
      a comb filter connected to the delta-sigma modulator and configured to output a difference between two of the plurality of samples in the delay line;
      an accumulator module comprising an accumulator connected to the comb filter, where the accumulator module is configured to integrate signals received from the comb filter during a non-delay-expansion period and transmit the integrated signals to the beamsummer during the non-delay expansion period, and where the accumulator module is configured to output a zero to the beamsummer during a delay-expansion period.

2. The delta-sigma beamformer of claim 1, wherein each delta-sigma modulator is configured to output a single bit delay line.

3. The delta-sigma beamformer of claim 1, wherein each delta-sigma modulator is configured to output a multi-bit delay line.

4. The delta-sigma beamformer of claim 1, where each accumulator module comprises a first multiplexer and a second multiplexer, and where the first multiplexer is connected to the comb filter and the accumulator, and wherein the first multiplexer is configured to pass a signal from the comb filter to the accumulator during the non-delay-expansion period, and where the first multiplexer is configured to output a zero and bypass the accumulator during the delay-expansion period, where the second multiplexer is connected to the accumulator and is configured to output a value of zero to the beamsummer during the delay-expansion period, and where the second multiplexer is configured to pass a signal from the accumulator to the beamsummer during a non-delay expansion period.

5. The delta-sigma beamformer of claim 1, wherein each comb filter is configured to adjust a distance in the delay line between the two of the samples during the delay-expansion period.

6. The delta-sigma beamformer of claim 5, wherein each comb filter is configured to adjust the distance in the delay line between the two of the samples to a shorter distance when adjusting a focus towards a near field.

7. The delta-sigma beamformer of claim 5, wherein each comb filter is configured to adjust the distance in the delay line between the two of the samples to a longer distance when adjusting a focus towards a far field.

8. An ultrasound imaging system comprising:
   a display screen;
   a beamsummer;
   a plurality of transducer elements arranged in an array;
   a plurality of channels, where each of the channels is configured to carry signals from one or more of the plurality of transducer elements;
   a plurality of delta-sigma modules, where each of the delta-sigma modules is connected to one of the plurality of channels, where each of the delta-sigma modules comprises:

a delta-sigma modulator configured to receive analog ultrasound signals from one of the plurality of channels and output a delay line including a plurality of samples based on the analog ultrasound signals;

a comb filter connected to the delta-sigma modulator and configured to output a difference between two of the plurality of samples in the delay line;

an accumulator module comprising an accumulator connected to the comb filter, where the accumulator module is configured to integrate signals received from the comb filter during a non-delay-expansion period and transmit the integrated signals to the beamsummer during the non-delay expansion period, and where the accumulator module is configured to output a zero to the beamsummer during a delay-expansion period.

9. The ultrasound imaging system of claim 8, wherein the display screen is either a touch screen or a multi-touch screen.

10. The ultrasound imaging system of claim 8, where the display screen and the beamsummer are disposed in a main module.

11. The ultrasound imaging system of claim 10, where the main module is adapted to be hand-held or hand-carried.

12. The ultrasound imaging system of claim 10, where the accumulator modules are disposed in a probe.

13. The ultrasound imaging system of claim 10, where the probe is a wireless probe adapted to transmit digital ultrasound data wirelessly to the main module.

14. The ultrasound imaging system of claim 8, where the plurality of transducer elements are grouped into a plurality of sub-apertures and where the delta-sigma modules perform sub-aperture processing for the sub-apertures.

15. The ultrasound imaging system of claim 8, where each of the comb filters is configured to adjust a distance in the delay line between the two of the samples during the delay-expansion interval.

16. A method for beamforming ultrasound signals, the method comprising:

providing analog ultrasound signals from a plurality of transducer elements to a delta-sigma modulator associated with one of a plurality of channels;

outputting a delay line from the delta sigma modulator, the delay line including a plurality of samples based on the analog ultrasound signals;

outputting, with a comb filter, a plurality of differences between samples at two different locations in the delay line;

providing the plurality of differences to an accumulator during a non-delay-expansion period;

generating an output signal with the accumulator during the non-delay-expansion period, where the output signal comprises an integration based on the plurality of differences;

providing the output signal to a beamsummer during the non-delay-expansion period;

activating a switch during a delay-expansion period, where activating the switch stops the plurality of differences from being sent to the accumulator during the delay-expansion period and causes a value of zero to be sent to the beamsummer during the delay-expansion period;

generating an image based on both the output signal and the value of zero provided to the beamsummer; and displaying the image.

17. The method of claim 16, where a spacing between the two of the plurality of different samples in the delay line is adjusted during the delay-expansion period according to a delay expansion interval.

18. The method of claim 16, where activating the switch comprises activating a multiplexer to cause a value of zero to be sent to the beamsummer during the delay-expansion period.

19. The method of claim 16, where generating the image is performed in a main module.

20. The method of claim 16, where generating the image is performed in a probe.

* * * * *